(12) United States Patent
Letendre et al.

(10) Patent No.: US 6,270,525 B1
(45) Date of Patent: Aug. 7, 2001

(54) PRECURSOR STENT GASKET FOR RECEIVING BILATERAL GRAFTS HAVING CONTROLLED CONTRALATERAL GUIDEWIRE ACCESS

(75) Inventors: Robert P. Letendre, Miami; Kenneth S. Solovay, Fort Lauderdale; Ivan A. Toyos, Miami, all of FL (US)

(73) Assignee: Cordis Corporation, Miami, FL (US)

( * ) Notice: Subject to any disclaimer, the term of this patent is extended or adjusted under 35 U.S.C. 154(b) by 0 days.

(21) Appl. No.: 09/404,660

(22) Filed: Sep. 23, 1999

(51) Int. Cl.$^7$ ........................................ A61F 2/06
(52) U.S. Cl. ............................ 623/1.35; 623/1.1
(58) Field of Search .................. 623/1.11, 1.12, 623/1.13, 1.18, 1.23, 1.31, 1.35, 1.24

(56) References Cited

U.S. PATENT DOCUMENTS

| | | | |
|---|---|---|---|
| 4,317,451 | 3/1982 | Cerwin et al. | 128/325 |
| 4,553,545 | 11/1985 | Maass | 128/341 |
| 4,580,568 | 4/1986 | Gianturco | 128/345 |
| 4,655,771 | 4/1987 | Wallsten | 623/1 |

(List continued on next page.)

FOREIGN PATENT DOCUMENTS

| | | | |
|---|---|---|---|
| 0 657 147 A2 | 10/1994 | (EP) | A61F/2/06 |
| WO 87/04935 | 8/1987 | (WO) | A61M/29/00 |
| WO 95/16406 | 6/1995 | (WO) | A61F/2/06 |
| WO 95/21592 | 8/1995 | (WO) | A61F/2/06 |
| WO 98/07389 | 2/1998 | (WO) | A61F/2/06 |
| WO 99/11199 | 3/1999 | (WO) | A61F/2/06 |

*Primary Examiner*—Bruce Snow
*Assistant Examiner*—Brian E Pellegrino

(57) ABSTRACT

A precursor stent for implantation within the body of a patient is utilized in combination with an aortic graft for repairing an abdominal aortic aneurysm. The stent is designed to receive a pair of grafts placed side by side within the interior of the stent. The stent includes a substantially cylindrical and expandable member having a proximal end, a distal end, a longitudinal axis extending therebetween and an interior. The stent further includes an occlusive member attached to the expandable member. The occlusive member at least partially occludes a passageway or stent lumen which extends through the interior of the expandable member extending between its distal end and proximal end. The occlusive member has an opening extending therethrough designed to receive a guidewire for one of the grafts. Therefore, when the guidewire for the other graft is introduced, after deployment of the stent within a body, it will go through the portion of the interior not covered by the occlusive member. This helps to ensure proper side by side placement of the two grafts.

16 Claims, 10 Drawing Sheets

U.S. PATENT DOCUMENTS

| | | | |
|---|---|---|---|
| 4,665,906 | 5/1987 | Jervis | 128/92 |
| 4,681,110 | 7/1987 | Wiktor | 128/343 |
| 4,732,152 | 3/1988 | Wallsten | 128/343 |
| 4,733,665 | 3/1988 | Palmaz | 128/343 |
| 4,739,762 | 4/1988 | Palmaz | 128/343 |
| 4,776,337 | 10/1988 | Palmaz | 128/343 |
| 4,784,137 | 11/1988 | Kulik et al. | 128/334 |
| 4,875,480 | 10/1989 | Imbert | 128/343 |
| 4,907,336 | 3/1990 | Gianturco | 29/515 |
| 4,950,227 | 8/1990 | Savin et al. | 604/8 |
| 4,990,151 | 2/1991 | Wallsten | 606/108 |
| 5,026,377 | 6/1991 | Burton et al. | 606/108 |
| 5,045,072 | 9/1991 | Castillo et al. | 604/280 |
| 5,159,920 | 11/1992 | Cordon et al. | 128/6 |
| 5,219,355 | 6/1993 | Parodi et al. | 606/191 |
| 5,304,197 | 4/1994 | Pinchuk et al. | 606/194 |
| 5,316,023 | 5/1994 | Palmaz et al. | 128/898 |
| 5,318,535 | 6/1994 | Miraki | 604/102 |
| 5,360,443 | 11/1994 | Barone et al. | 623/1 |
| 5,411,507 | 5/1995 | Heckele | 606/108 |
| 5,476,506 | 12/1995 | Lunn | 623/1 |
| 5,480,423 | 1/1996 | Ravenscroft et al. | 623/1 |
| 5,484,444 | 1/1996 | Braunchweiler et al. | 606/108 |
| 5,507,769 | 4/1996 | Marin et al. | 606/198 |
| 5,522,880 | 6/1996 | Barone et al. | 623/1 |
| 5,562,724 | 10/1996 | Vorwerk et al. | 623/1 |
| 5,571,170 | 11/1996 | Palmaz et al. | 623/1 |
| 5,571,171 | 11/1996 | Barone et al. | 623/1 |
| 5,571,173 | 11/1996 | Parodi | 623/1 |
| 5,578,071 | 11/1996 | Parodi | 623/1 |
| 5,578,072 | 11/1996 | Barone et al. | 623/1 |
| 5,591,229 | 1/1997 | Parodi | 623/1 |
| 5,617,878 * | 4/1997 | Taheri | 623/1.13 |
| 5,628,788 | 5/1997 | Pinchuk | 623/1 |
| 5,632,763 | 5/1997 | Glastra | 606/194 |
| 5,639,278 | 6/1997 | Dereume et al. | 623/1 |
| 5,653,745 | 8/1997 | Trescony et al. | 623/1 |
| 5,676,696 | 10/1997 | Marcade | 623/1 |
| 5,683,449 | 11/1997 | Marcade | 623/1 |
| 5,693,084 | 12/1997 | Chuter | 623/1 |
| 5,702,418 | 12/1997 | Ravenscroft | 606/198 |
| 5,749,880 | 5/1998 | Banas et al. | 606/198 |
| 5,760,006 | 6/1998 | Shank et al. | 514/23 |
| 5,824,040 * | 10/1998 | Cox et al. | 606/194 |
| 5,824,042 | 10/1998 | Lombardi et al. | 623/1 |
| 5,824,055 * | 10/1998 | Spiridigliozzi et al. | 623/1.11 |
| 5,843,160 * | 12/1998 | Rhodes | 623/1.35 |
| 5,855,598 | 1/1999 | Pinchuk | 623/1 |
| 5,980,565 | 11/1999 | Jayaraman | 623/1 |
| 5,993,481 | 11/1999 | Marcade et al. | 623/1 |
| 6,039,749 | 3/2000 | Marin et al. | 606/198 |
| 6,070,589 | 6/2000 | Keith et al. | 128/898 |

* cited by examiner

PRECURSOR STENT GASKET FOR RECEIVING BILATERAL GRAFTS HAVING CONTROLLED CONTRALATERAL GUIDEWIRE ACCESS

FIELD OF THE INVENTION

The invention relates to a precursor stent gasket, for use with an aortic graft for repairing an abdominal aortic aneurysm.

BACKGROUND OF THE INVENTION

An abdominal aortic aneurysm is a sac caused by an abnormal dilation of the wall of the aorta, a major artery of the body, as it passes through the abdomen. The abdomen is that portion of the body which lies between the thorax and the pelvis. It contains a cavity, known as the abdominal cavity, separated by the diaphragm from the thoracic cavity and lined with a membrane, the peritoneum. The aorta is the main trunk, or artery, from which the systemic arterial system proceeds. It arises from the left ventricle of the heart, passes upward, bends over and passes down through the thorax and through the abdomen to about the level of the fourth lumbar vertebra, where it divides into the two common iliac arteries.

The aneurysm usually arises in the infrarenal portion of the diseased aorta, for example, below the kidneys. When left untreated, the aneurysm will eventually cause rupture of the sac with ensuing fatal hemorrhaging in a very short time. High mortality associated with the rupture has led to the present state of the art and the trans-abdominal surgical repair of abdominal aortic aneurysms. Surgery involving the abdominal wall, however, is a major undertaking with associated high risks. There is considerable mortality and morbidity associated with this magnitude of surgical intervention, which in essence involves replacing the diseased and aneurysm segment of blood vessel with a prosthetic device which typically is a synthetic tube, or graft, usually fabricated of either DACRON®, TEFLON®, or other suitable material.

To perform the surgical procedure requires exposure of the aorta through an abdominal incision, which can extend from the rib cage to the pubis. The aorta must be closed both above and below the aneurysm, so that the aneurysm can then be opened and the thrombus, or blood clot, and arteriosclerotic debris removed. Small arterial branches from the back wall of the aorta are tied off, The DACRON® tube, or graft, of approximately the same size of the normal aorta is sutured in place, thereby replacing the aneurysm. Blood flow is then reestablished through the graft. It is necessary to move the intestines in order to get to the back wall of the abdomen prior to clamping off the aorta.

If the surgery is performed prior to rupturing of the abdominal aorta aneurysm, the survival rate of treated patients is markedly higher than if the surgery is performed after the aneurysm ruptures, although the mortality rate is still quite high. If the surgery is performed prior to the aneurysm rupturing, the mortality rate is typically less than 5%. Conventional surgery performed after the rupture of the aneurysm is significantly higher, one study reporting a mortality rate of 66.7%. Although abdominal aortic aneurysms can be detected from routine examinations, the patient does not experience any pain from the condition. Thus, if the patient is not receiving routine examinations, it is possible that the aneurysm will progress to the rupture stage, wherein the mortality rates are significantly higher.

Disadvantages associated with the conventional, prior art surgery, in addition to the high mortality rate, are: the extended recovery period associated with such surgery; difficulties in suturing the graft, or tube, to the aorta; the loss of the existing thrombosis to support and reinforce the graft; the unsuitability of the surgery for many patients having abdominal aortic aneurysms; and the problems associated with performing the surgery on an emergency basis after the aneurysm has ruptured. As to the extent of recovery, a patient can expect to spend from 1 to 2 weeks in the hospital after the surgery, a major portion of which is spent in the intensive care unit, and a convalescence period at home from 2 to 3 months, particularly if the patient has other illness such as heart, lung, liver, and/or kidney disease, in which case the hospital stay is also lengthened. Since the graft must be secured, or sutured, to the remaining portion of the aorta, it is often difficult to perform the suturing step because of thrombosis present on the remaining portion of the aorta, and that remaining portion of the aorta wall may be friable, or easily crumbled.

Since the thrombosis is totally removed in the prior art surgery, the new graft does not have the benefit of the previously existing thrombosis therein, which could be utilized to support and reinforce the graft, were the graft to be able to be inserted within the existing thrombosis. Since many patients having abdominal aortic aneurysms have other chronic illnesses, such as heart, lung, liver, and/or kidney disease, coupled with the fact that many of these patients are older, the average age being approximately 67 years old, these patients are not ideal candidates for such surgery, which is considered major surgery. Such patients have difficulties in surviving the operation. Lastly, once the aneurysm has ruptured, it is difficult to perform a conventional surgery on an expedited basis because of the extent of the surgery.

Accordingly, the prior art teaches various methods and apparatus for repairing an abdominal aortic aneurysm which is believed to lower morbidity and mortality rate by not requiring an abdominal incision and general anesthesia, not requiring suturing the graft to the remaining aortic wall, and which permits the existing aortic wall and thrombosis therein to be retained to reinforce and support the aortic graft. An example of such a method and apparatus is given in U.S. Pat. No. 5,316,023 issued to Palmaz et al. on May 31, 1994; U.S Pat. No. 5,360,443 issued to Barone et al. on Nov. 1, 1994; U.S. Pat. No. 5,578,071 issued to Parodi on Nov. 26, 1996; and U.S. Pat. No. 5,591,229 issued to Parodi on Jan. 7, 1997, all of which are hereby incorporated herein by reference.

Devices, such as the one shown in the above referenced Barone patent, use an improved method for repairing an abdominal aortic aneurysm in an aorta having two iliac arteries associated therewith. The device includes first and second tubes, preferably made from a variety of materials such as DACRON® and other polyester materials, TEFLON® (polytetrafluoroethylene), TEFLON® coated DACRON®, porous polyurethane, silicone, expanded polytetrafluoroethylene, and expanded polyurethane. It is preferred that all of the foregoing materials be porous to allow for an intimal layer to form on the tubes 160. Each of the tubes are connected to expandable and deformable, tubular members, or stents. These stents can be similar in structure to those described in disclosed in U.S. Pat. No. 4,733,665 issued on Mar. 29, 1988; U.S. Pat. No. 4,739,762, issued on Apr. 26, 1988; and U.S. Pat. No. 4,776,337 issued on Oct. 11, 1988, all of the foregoing patents being in the name of Julio C. Palmaz, each of which is incorporated herein by reference. Each of the tube/stent structures are then disposed on the end of a balloon catheter. Either both tubes are inserted into the same femoral artery or one of the tubes is inserted into one femoral artery of the patient and the other tube is inserted into the other femoral artery of the patient. Thereafter the tubes are intraluminally delivered to the aorta, thereby disposing at least a portion of each tube within the abdominal aortic aneurysm. The balloon catheters are then expanded to expand and deform the tubular members, to force the tubular members radially outwardly into contact with the aorta and each other. This secures the tubular members and a least a portion of each tube within the aorta, whereby the tubes provide a bilateral fluid passageway through the abdominal aortic aneurysm.

While the above mentioned devices would seem to work well, there is a desire to improve upon the device. More particularly, there was a need to ensure that most of the blood flowing through the abdomen, flows through the bilateral fluid passageways and not around them where it could cause further damage. The precursor stent gasket described in U.S. patent application Ser. No. 09/050,347, filed on Mar. 30, 1998, and U.S. patent application Ser. No. 09/188,582, filed on Nov. 9, 1998, the disclosures of which are hereby incorporated herein by reference, limits the amount of blood which could leak around the bilateral fluid passageways and into the aneurysm. The pre-cursor stent is positioned within the infrarenal neck, between an abdominal aortic aneurysm and the renal arteries, of a patient to assist in repairing the abdominal aortic aneurysm. The stent is designed to be coupled to the bilateral grafts for directing blood flow. The graft has a distal end for positioning distal to the aneurysm, and a proximal end for positioning proximal to the aneurysm. The precursor stent includes a substantially cylindrical expandable member having a proximal end, a distal end and an interior. The stent further includes a compressible gasket member located within the interior of the expandable member and attached thereto. The compressible member is substantially impervious to blood when in a compressed state. In addition, the stent has a means, within the compressible member, for coupling the graft to the gasket member. This is so the coupled device can direct blood flow through the graft, with the gasket member substantially preventing blood from flowing into the aneurysm.

The precursor stent gasket described above is delivered by a delivery system which is guided by a guidewire, such as a steerable coronary angioplasty guidewire. The guidewire typically extends through the delivery system and through the one side precursor stent gasket to extend distally of the delivery system. After the precursor stent gasket has been deployed, the delivery system is removed. However, the guidewire is often left in place so as to guide one of the bilateral grafts into position with respect to the precursor stent gasket. However, the physician must place a second guidewire, contralateral to the first, through the precursor stent gasket. This can be difficult, and can require precise control of the second guidewire. Therefore, there has been a need for a precursor stent gasket which can easily guide the second guidewire into position. The present invention provides for such a device.

SUMMARY OF THE INVENTION

In accordance with the present invention there is provided a precursor stent for implantation within the body of a patient, particularly for treating abdominal aortic aneurysms. The stent is designed to receive a pair of grafts placed side by side within the interior of the stent. The stent includes a substantially cylindrical and expandable member having a proximal end, a distal end, a longitudinal axis extending therebetween and an interior. The stent further includes an occlusive member attached to the expandable member. The occlusive member at least partially occludes a passageway or stent lumen which extends through the interior of the expandable member extending between its distal end and proximal end. The occlusive member has an opening extending therethrough designed to receive a guidewire for one of the grafts. Therefore, when the guidewire for the other graft is introduced, after deployment of the stent within a body, it will go through the portion of the interior not covered by the occlusive member. This helps to ensure proper side by side placement of the two grafts.

BRIEF DESCRIPTION OF DRAWINGS

The foregoing and other aspects of the present invention will best be appreciated with reference to the detailed description of the invention in conjunction with the accompanying drawings, wherein.

DETAILED DESCRIPTION OF THE INVENTION

Figure 12:
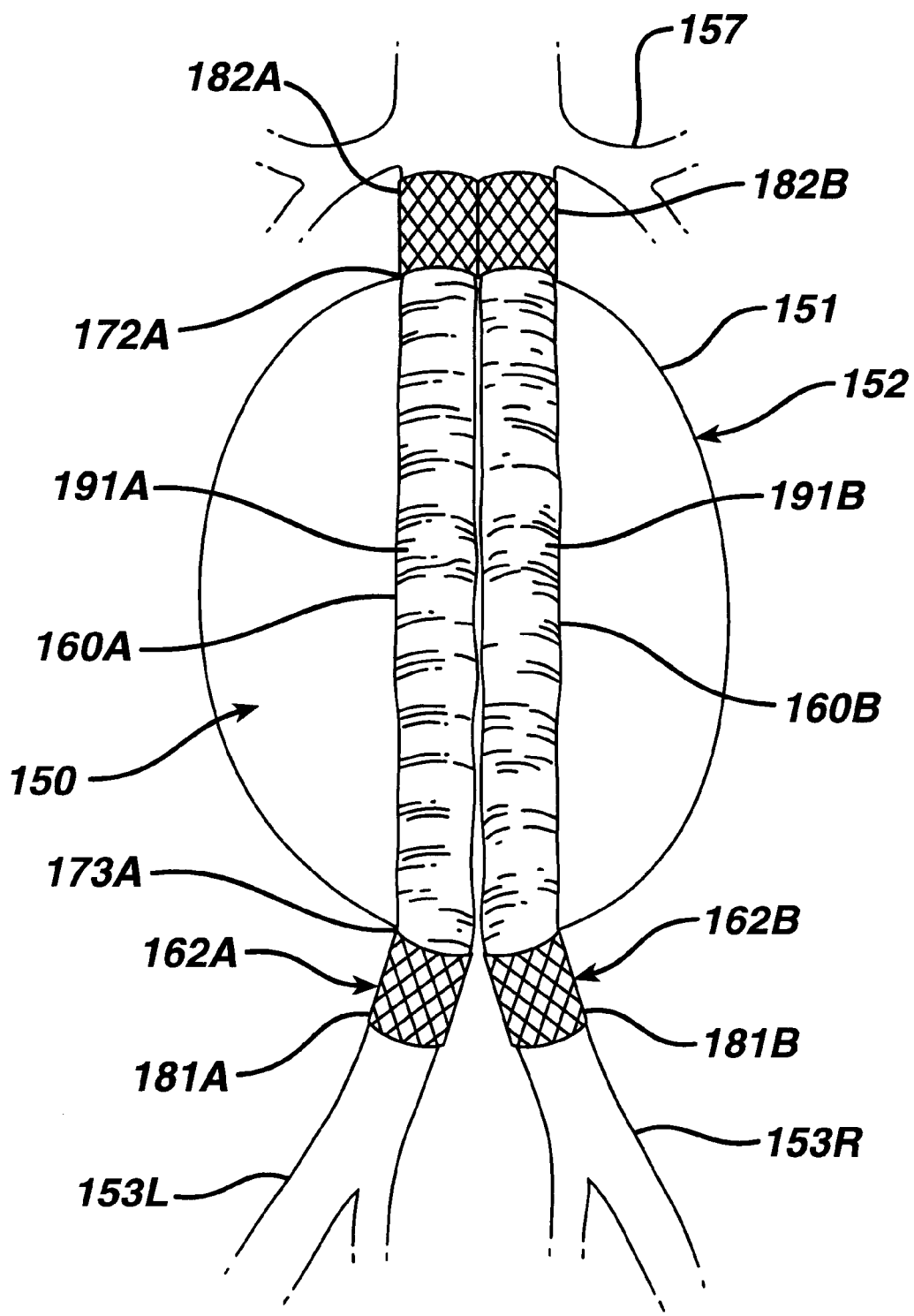
FIG. 12 is a view similar to that of FIG. 8, but showing a prior art bilateral graft system.

The present invention is designed to be coupled and/or used with a graft for directing blood flow. Referring now to the drawings, wherein like numerals indicate the same element throughout the views, there is shown in FIG. 12, a prior art version of such a graft. The type of graft it is designed to be coupled to is very similar to types of grafts known in the prior art. Therefore, a description of a prior art graft may be helpful. FIG. 12 shows such a graft. FIG. 12 shows a bilateral intra-aortic bypass graft 150 for intraluminal delivery to repair an abdominal aortic aneurysm 151 in an aorta 152 having two iliac arteries 153L, 153R associated therewith. Associated with aorta 152, above aneurysm 151, are a plurality of renal arteries 157, in fluid communication with aorta 152. Bilateral intra-aortic bypass graft 150, as well as other grafts to be hereinafter described, could also be utilized in the thoracic aorta, and can be used to repair thoracic aneurysms or thoracic dissecting aneurysms. Accordingly, use of the term "aortic aneurysm" in this specification and claims is intended to relate to and mean both abdominal aortic aneurysms and thoracic aneurysms Bypass graft 150 is seen to generally comprise a first graft tube 160A having distal and proximal ends 172A and 173A, at least a portion of the graft tube 160A adapted to be disposed within the aneurysm 151, preferably so that its distal end is distal to the aneurysm and its proximal end is proximal to the aneurysm. A second graft tube 160B is similarly situated on the right side. Graft 150 also includes first and second tubular stent members 162A, 162B, each having proximal and distal ends 181A & 181B, and 182A & 182B located within grafts 160. Each stent member 162A, 162B has proximal and distal ends, preferably positioned so that the distal ends are distal to the aneurysm and the proximal ends are proximal to the aneurysm.

The stent members 162, along with graft tubes 160 permit intraluminal delivery into the aorta 152. This is accomplished by percutaneously inserting the stent members into the same or different femoral arteries and navigating them into the aorta. This type of procedure is similar to delivery of angioplasty catheters and guiding catheters into the human vasculature. Upon the placement of the stent members they are deployed either through a radially, outwardly extending force, such as a balloon catheter, or self-expanding stents and deployed by releasing the stent members from a constraint. Once deployed, a bilateral passageway is formed within the abdominal aortic aneurysm by passageways 191A, 191B extending through the stent members 162 and graft tubes 160 forming a generally inverted Y-shaped configuration. Each stent member 162A, 162B preferably has a smooth outer wall surface disposed between its distal and proximal ends. Stent members 162 preferably have a substantially uniform thickness with a plurality of slots formed therein.

Graft tubes 160A, 160B preferably have a generally, circular cross-sectional configuration, and can be made from a variety of materials, provided they have the requisite strength characteristics to be utilized as a bypass graft 150, as well as have the requisite compatibility with the human body in order to be used as a graft, or implant material, without being rejected by the patient's body. Examples for such materials are DACRON Registered™ and other polyester materials, TEFLON Registered™ (polytetrafluoroethylene), TEFLON Registered™ coated DACRON Registered ™, porous polyurethane, silicone, expanded polytetrafluoroethylene, and expanded polyurethane. It is preferred that all of the foregoing materials be porous to allow for an intimal layer to form on the graft tubes 160. Additionally, graft tubes 160A, 160B can be made by the replamineform replicated life forms process, which is a method for fabricating uniformly microporous materials from marine skeletal structures. The foregoing described fabric materials can be knitted or woven, and can be warp or weft knitted. If the material is warp knitted, it may be provided with a velour, or towel like surface, which speeds up clotting of blood which contacts graft tubes 160A, 160B in order to increase the attachment, or integration, of graft tubes 160A, 160B to aorta 152, or to assist the integration of graft tubes 160A, 160B to the thrombosis 154. Graft tubes 160A, 160B can also be made of a biodegradable, or degradable material, such as albumin or collagen or a collagen coated material. A graft tube which is bioerodible, would erode and dissolve, or degrade, over a period of time; however, it is believed that a layer of endothelium, or skin, will grow as the graft tubes 160A, 160B erode, the new layers of endothelium, or skin, provide a new, fluid impervious lining within aneurysm 151. In some procedures, it might be desirable to make graft tubes 160A, 160B of a fluid impervious material. Additionally, graft tubes 160A, 160B or stent 162A, 162B, could have a coating of a biologically inert material, such as TEFLON Registered™ or porous polyurethane.

If any of the foregoing described materials are used for the manufacture of graft tubes 160, the graft tubes may be connected to the stent members 162 as by a plurality of conventional sutures of polypropylene, DACRON Registered™, or any other suitable material. Preferably, the ends of graft tubes 160 overlap and fully cover the second ends of stent members 162, such overlapping being approximately 100% of the length of stent members 162.

Figure 1:
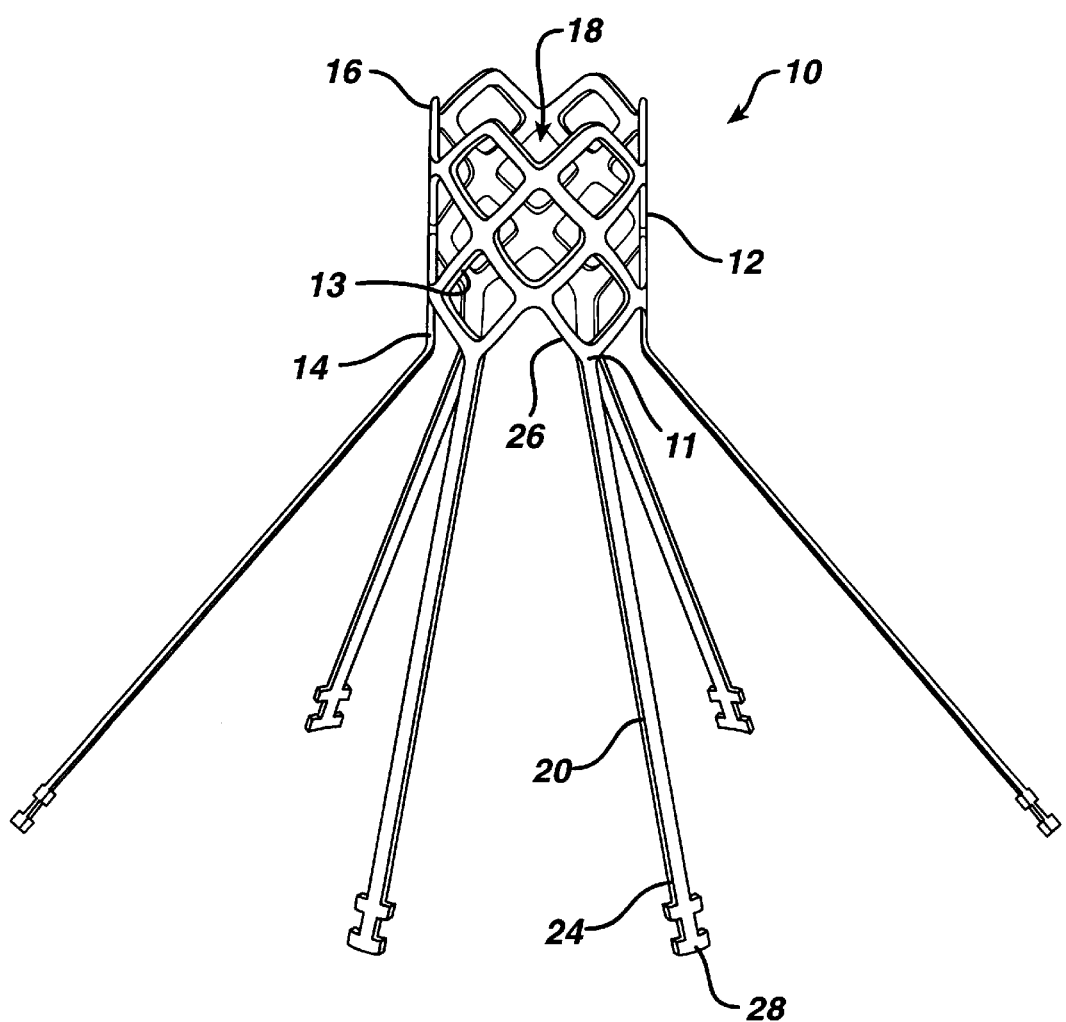
FIG. 1 is a perspective view of one preferred embodiment of precursor stent 10 made in accordance with the present invention having the gasket member 30, and occlusive member 100 removed for clarity.

The present invention improves upon the prior art graft 150, mentioned above, by further including, and preferably initially deploying, a precursor stent 10, shown in FIG. 1. Stent 10 is to be deployed within the infrarenal neck, between an abdominal aortic aneurysm and the renal arteries of a patient to assist in repairing the abdominal aortic aneurysm. The stent is designed to be coupled to a graft, such as the one described above, for directing blood flow through the aneurysm. The stent is made from a substantially cylindrical self-expanding member 12 having a proximal end 14, a distal end 16, a longitudinal axis extending therebetween and an interior 18. The precursor stent further includes at least two, but preferably 8 as shown in FIG. 1, spaced apart longitudinal legs 20 each having proximal and distal ends 24 and 26 respectively. Preferably, there is a leg extending from each apex 11 of diamonds 13. The distal ends 26 of the legs are attached to the proximal end 14 of the member 12, the legs extending proximally away from the member. At least one, but preferably each leg includes a flange 28 adjacent its proximal end which, as is described in greater detail below, allows for the stent to be retrievable into its delivery apparatus after partial or full deployment of member 12 so that it can be turned, or otherwise repositioned for proper alignment.

Self expanding stents are typically made from superelastic Nickel Titanium alloys (Nitinol). Descriptions of medical devices which use such alloys can be found in U.S. Pat. No. 4,665,906 issued to Jervis on May 19, 1987, which is hereby incorporated herein by reference. Stent 10 is preferably laser cut from a tubular piece of Nickel Titanium Alloy and thereafter treated so as to exhibit superelastic properties at body temperature. Stent 10 is shown in the figures as being a diamond patterned stent, having approximately 8 diamonds, and when the stent is fully expanded the diamonds would have angles of 45–55 degrees at their distal and proximal ends. However, stent 10 can take on many different patterns or configurations.

Figure 2:
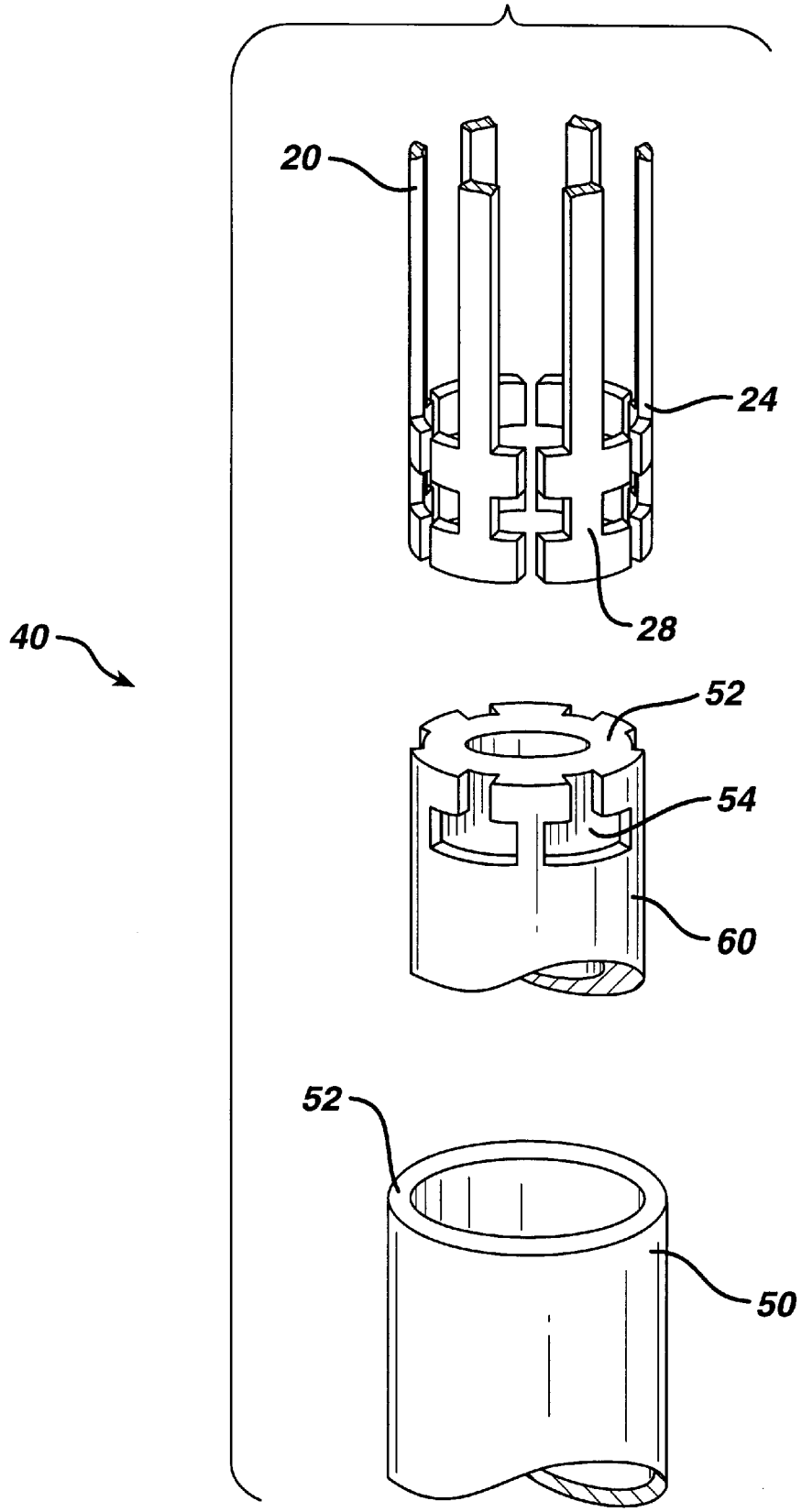
FIG. 2 is a partial exploded view of the distal end of an apparatus 40 for delivering a precursor stent made in accordance with the present invention, and also shows the legs and flanges of the precursor stent.
Figure 3:
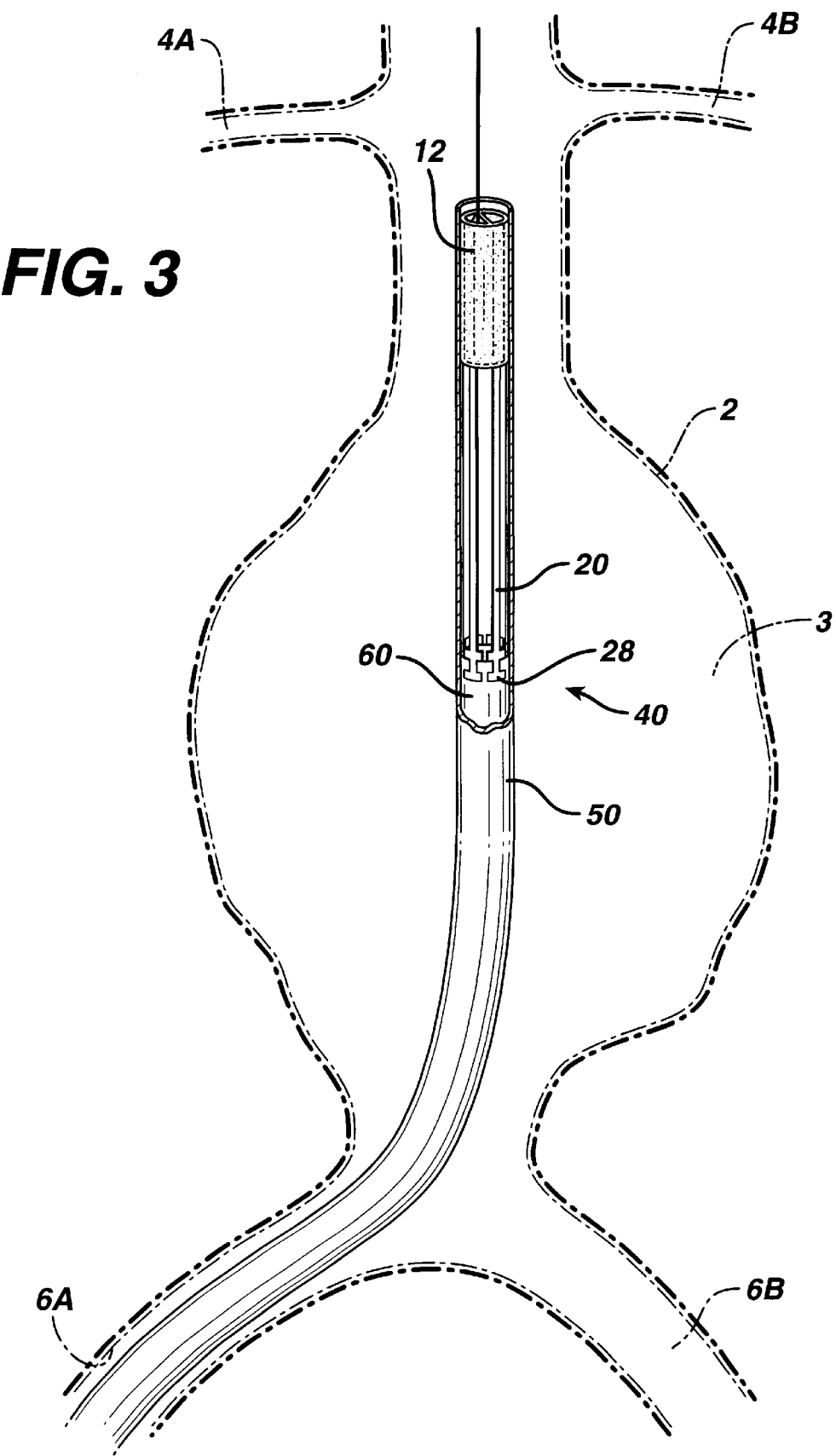
FIG. 3 is a simplified cross sectional view of an abdominal aortic aneurysm showing apparatus 40 inserted therein with precursor stent in its fully un-deployed position.

Many of the advantages of stent 10 can be better understood by referring to its delivery apparatus 40 shown in FIGS. 2 and 3. Apparatus 40 includes an outer sheath 50 which is essentially an elongated tubular member, similar to ordinary guiding catheters which are well known to those of ordinary skill in the art. Sheath 50 has a distal end 52 and a proximal end (not shown). Apparatus 40 also includes an inner shaft 60 located coaxially within the outer sheath 50 prior to deployment as shown in FIG. 3. The inner shaft has a distal end 52 and a proximal end. (not shown). The distal end 52 of the shaft has at least two, preferably eight to match the number of longitudinal arms and diamond apexes on stent 10, grooves 54 disposed thereon. As seen from FIG. 3, when the apparatus is not fully deployed the stent 10 is located within the outer sheath 50 and makes frictional contact therewith. The flanges 28 on the legs 20 of the stent 10 are set within the grooves 54 of the inner shaft 60, thereby releasably attaching the stent 10 to the inner shaft 60.

Figure 4:
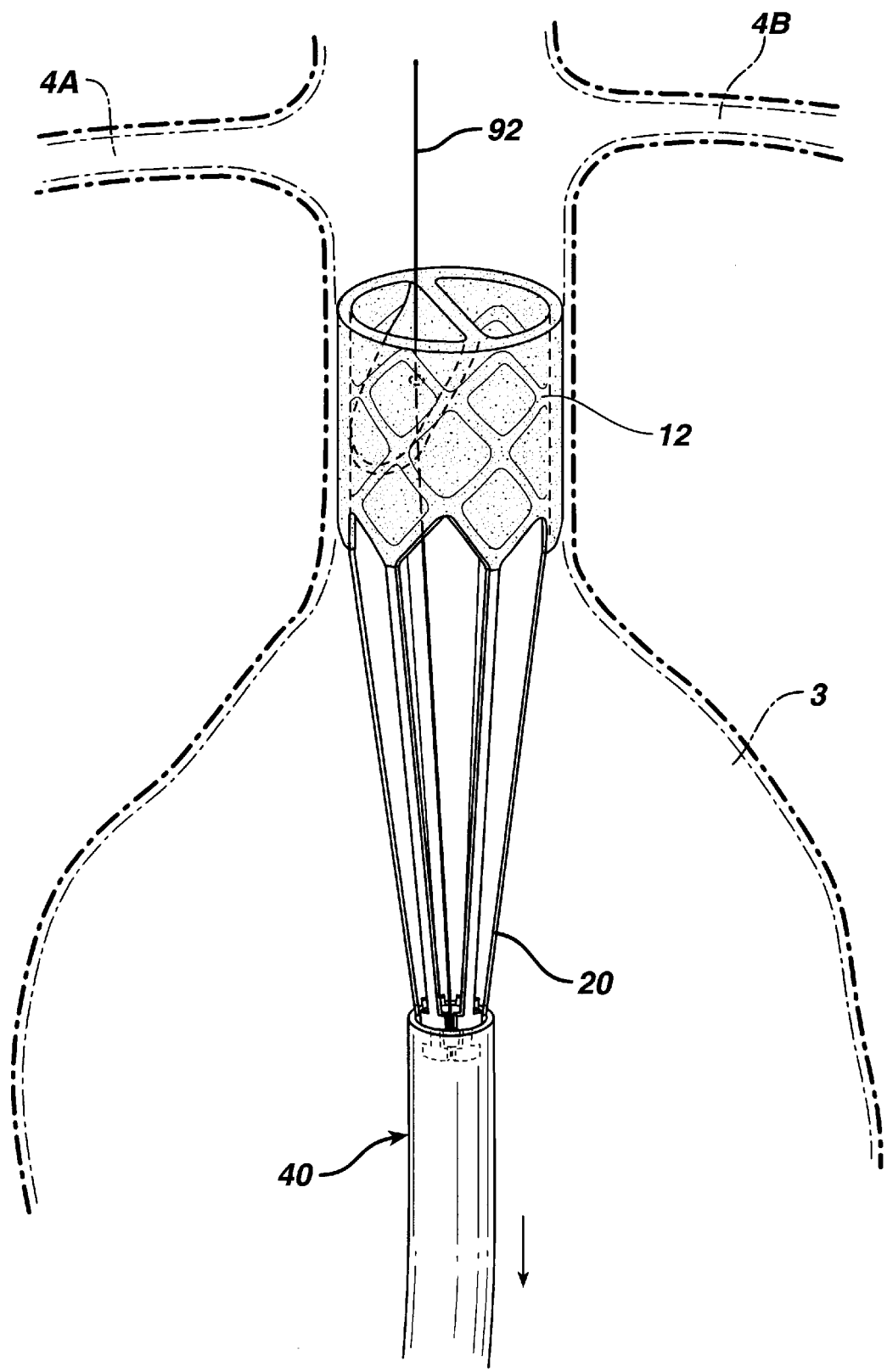
FIG. 4 is a view similar to that of FIG. 3 but showing the precursor stent in its partially deployed position.

The advantages of the longitudinal legs 20, its flanges 28 and the grooves 54 on the inner shaft 60 can best be described by referring to FIGS. 3 and 4. FIG. 3 shows the apparatus 40 with the stent in its fully un-deployed position. FIG. 3 also shows an aorta 2, an abdominal aortic aneurysm 3, renal arteries 4A and 4B, and iliac vessels 6A and 6B of a human patient. As seen from FIG. 3, the apparatus 40 has been percutaneously inserted into the femoral artery and guided within the patients vascular system and inserted into the aneurysm 3. As mentioned above, expandable member 12 of stent 10 is designed to be deployed within the infrarenal neck, between an abdominal aortic aneurysm and the renal arteries of a patient to assist in repairing the abdominal aortic aneurysm. As will become apparent below when discussing the gasket aspect of the present invention, placement of expandable the member 12 is important. The physician must achieve precise placement of the member to ensure adequate repair of the aneurysm.

As seen from FIG. 4, the present invention allows the physician to fully deploy member 12 within the body without fully releasing the entire stent 10 from engagement with the delivery apparatus 40. The legs 20 of the stent interlock with grooves 54 on inner shaft 60. Therefore, if the physician decides that the placement of the stent 10 as shown in FIG. 4 is incorrect, he or she would then push on the outer member of the apparatus 40 while keeping the inner member stationary, thereby resulting in the stent 10 being retrieved or retracted within outer sheath 50 so that the physician could reposition the stent 10. The legs 20 allow the physician to see how the member 12 would be positioned when fully deployed. Once the physician has achieved the desired position for the member 12, the legs 20 are released from their engagement with the inner shaft 60 and moved away from member 12 so as not to interfere with the rest of the procedure, as shown by the arrows in FIG. 5. The legs 20 are very pliable and do not need to be pushable, so that they are as a traumatic as possible.

In order to prevent the physician from prematurely completing deployment of the stent 10, a releasable stop is preferably placed on the inner shaft 60. The stop could be a ring having a greater diameter than the outer member, so that as the outer member is pulled proximally along the inner shaft it hits the stop, and prevents full deployment of the entire stent 10. The stop is preferably releasably attached to the inner member, by threads or the like, so that it can be released from its engagement with the inner shaft to allow the outer member to slide back enough to fully deploy the entire stent 10 within the body.

Figure 10:
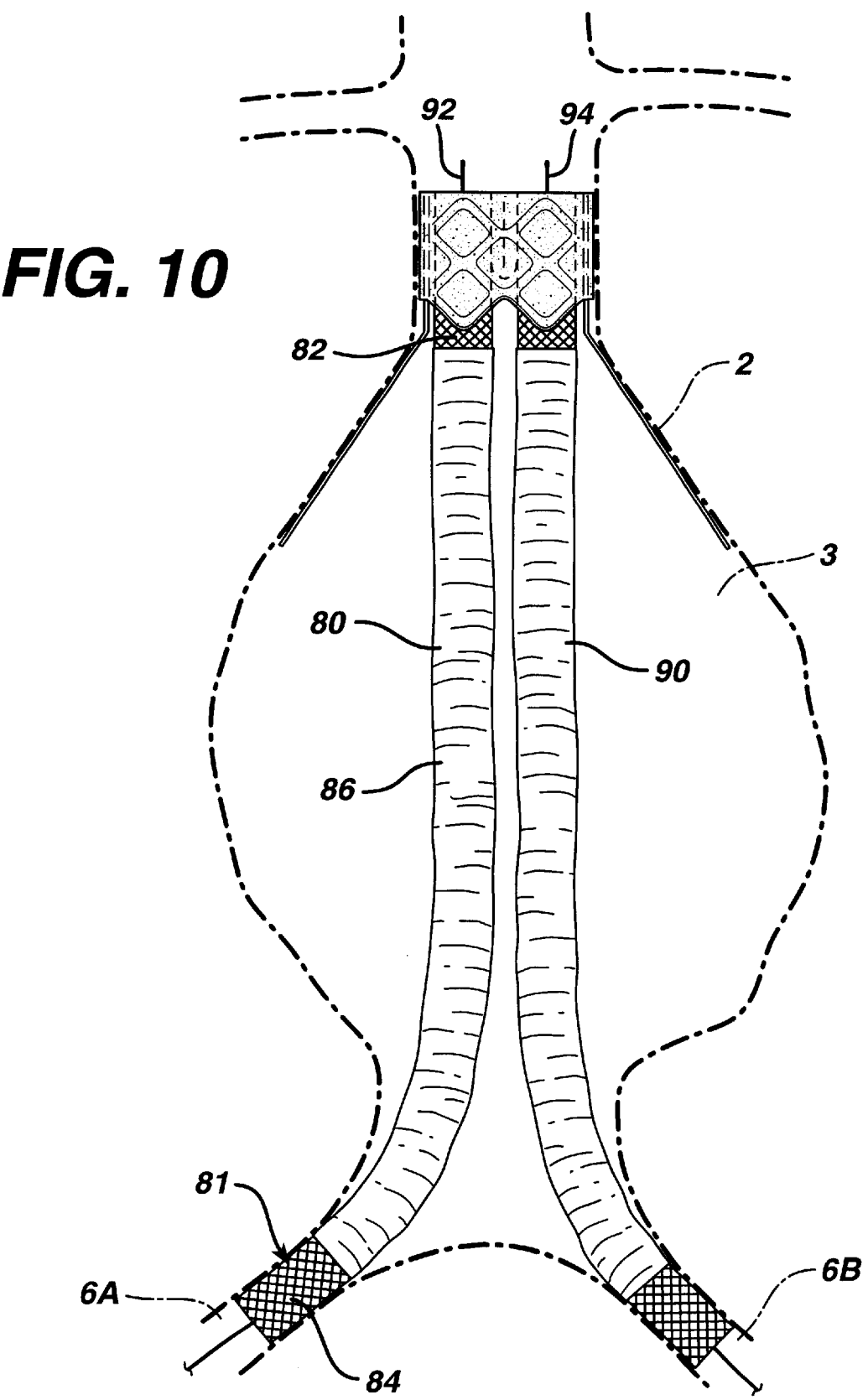
FIG. 10 is a view similar to that of FIG. 5 but showing the precursor stent 10 coupled to endografts.

In one embodiment exemplary of the precursor stent 10, shown in most of the figures but removed from FIG. 1 for clarity, precursor stent 10 further includes a gasket member 30. This feature can be better understood by referring to FIG. 6. Gasket member 30 surrounds the member 12 and can be located along the interior of member 12, the exterior of member 12 or both. The gasket member 30 helps impede any blood trying to flow around graft members 80 and 90 after they have been inserted (as shown in FIG. 10) and from flowing around the precursor stent itself. For this embodiment, gasket member 30 comprises a compressible member located along both the interior and the exterior of expandable member 12. For the embodiment shown in FIG. 6, gasket member 30 can be made from any number of materials known to those of ordinary skill in the art including open cell foam materials such as polyurethane, polyethylene, polytetrafluoroethylene, Other various polymer materials which are woven or knitted to provide a flexible structure such as Dacron, polyurethane, polypropylene, polytetrafluoroethylene can also be used. Highly compressible foams are particularly preferred, so as to keep the crimped profile low for better delivery. Gasket 30 can be attached to expandable member 12 by any number of means including a plurality of conventional sutures of polypropylene, DACRON®, or any other suitable material. Other methods of attaching gasket 30 to expandable member include adhesives, ultrasonic welding, mechanical interference fit and staples.

As will be explained subsequently, it is preferable that the compressible member is substantially impervious to the flow of blood, at least when in a partially compressed state. When used throughout for the present invention, materials which are substantially impervious to the flow of blood include materials which become substantially impervious to the flow of blood after being saturated with blood. When the stent tubes and graft members, described above, are inserted and expanded within the gasket 30, the gasket 30 will compress. In this state, the gasket should be substantially impervious to blood so as to prevent blood from flowing through the interior 26 of member 12 and into the aneurysm.

Figure 6:
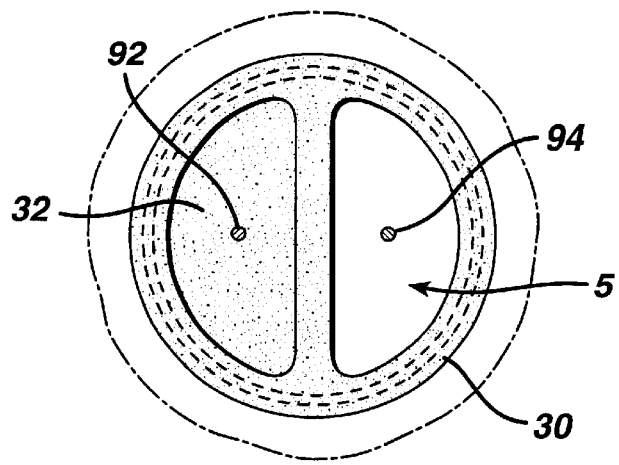
FIG. 6 is a partial cross sectional view taken along line 6—6 of FIG. 5.
Figure 7:
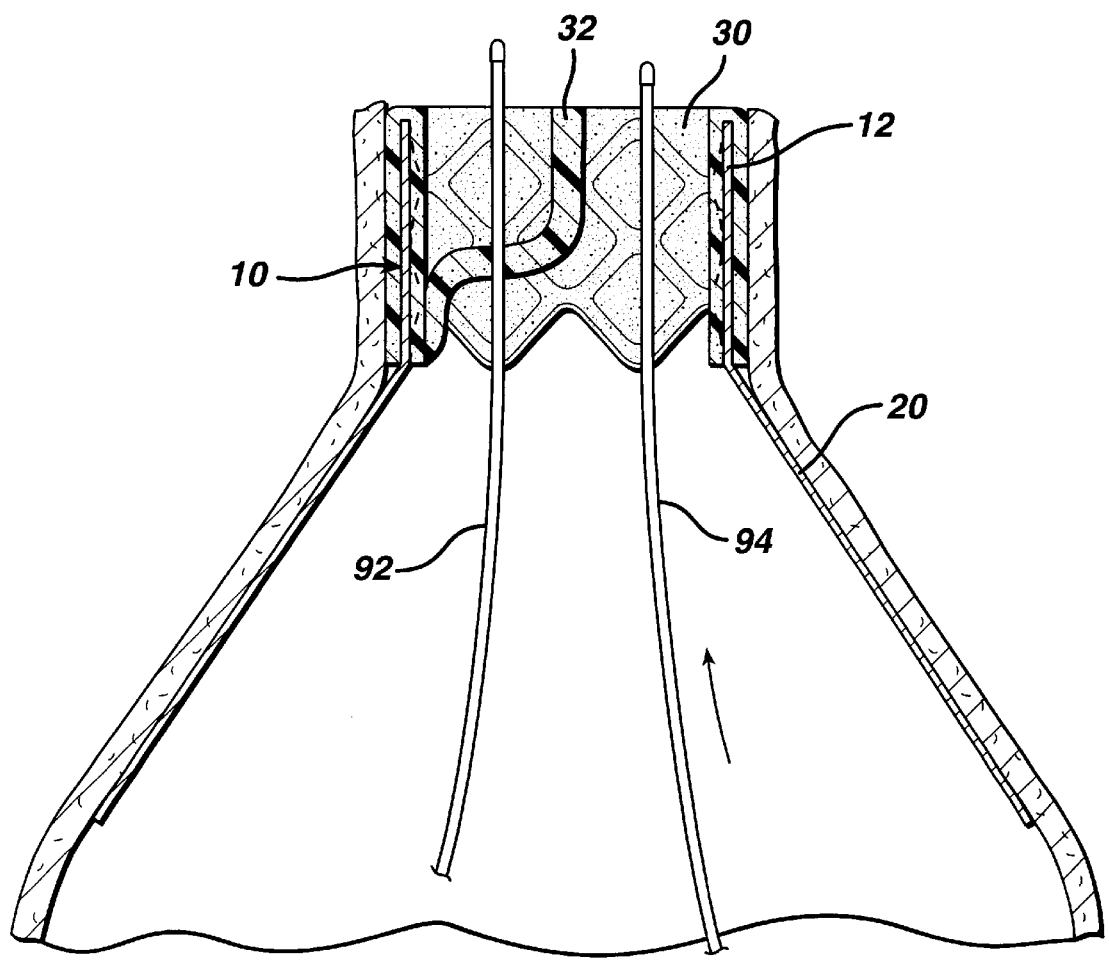
FIG. 7 is a partial cross sectional view taken along line 7—7 of FIG. 5.

As seen from FIGS. 6 and 7, the precursor stent further includes an occlusive member 32 attached to the expandable member 12. The occlusive member 32 covers a predetermined portion of the interior of the expandable member 12. The occlusive member 32 covers the interior of the expandable member 12 in such a way that a lumen 5 of the expandable member 12 which provides a passageway from its proximal end 14 to its distal end 16 is partially blocked (as best illustrated in FIG. 6). Preferably, the cover blocks about one half of the lumen as taken from a cross section of the expandable member perpendicular to its longitudinal axis. Occlusive member 32 further includes an opening extending therethrough so as to receive a guidewire 92 for guiding stent graft 80 to the target site. Thereafter, when guidewire 94 for the graft 90 is introduced, the occlusive member 32 will prevent it from going on the same half that guidewire 92 is positioned, and will force it to go through the other half of the interior of the stent gasket. This helps to ensure proper side by side placement of the two grafts.

Figure 5:
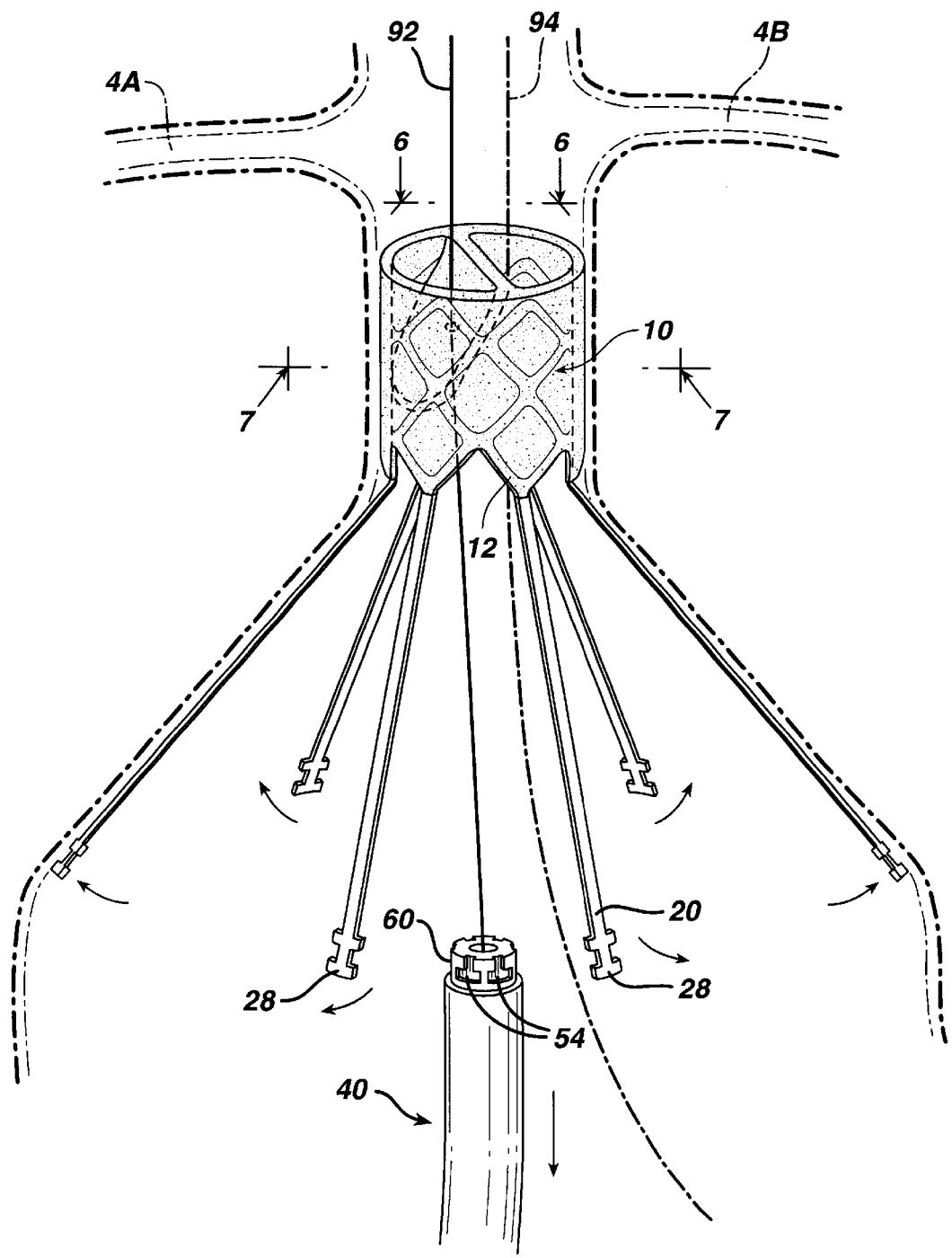
FIG. 5 is a view similar to that of FIG. 4 but showing the precursor stent in its fully deployed position and also showing, in phantom, placement of the second guidewire.

To begin, the physician would percutaneously insert apparatus 40 into one of a patients femoral arteries and guide the apparatus into the abdominal aorta. Thereafter, as seen from FIG. 4, stent gasket 10 is inserted into the body and delivered to the target site with the help of guidewire 92. Once the physician has achieved proper position of the stent gasket 10, it is released fully from the sheath 40, and appears as shown in FIG. 5. As seen from that figure, guidewire 92 remains in position upon full deployment of stent gasket 10. Once the stent gasket has been deployed the physician would then gain access to the patients other femoral artery and insert another guidewire 94 into the patients abdominal aorta, as shown in phantom on FIG. 5. If guidewire 94 is on the wrong side of the interior of stent 10, it will hit occlusive member 32. The physician will feel this with his hands and know that he has not yet achieved proper placement of the second guidewire 94. The physician may then go through a series of motions where he steers and pushes the guidewire 94, until he no longer feels interference from occlusive member 32 and the guidewire passes through the opening in the stent 10, and this will let him know he has achieved proper placement of the second guidewire.

Figure 8:
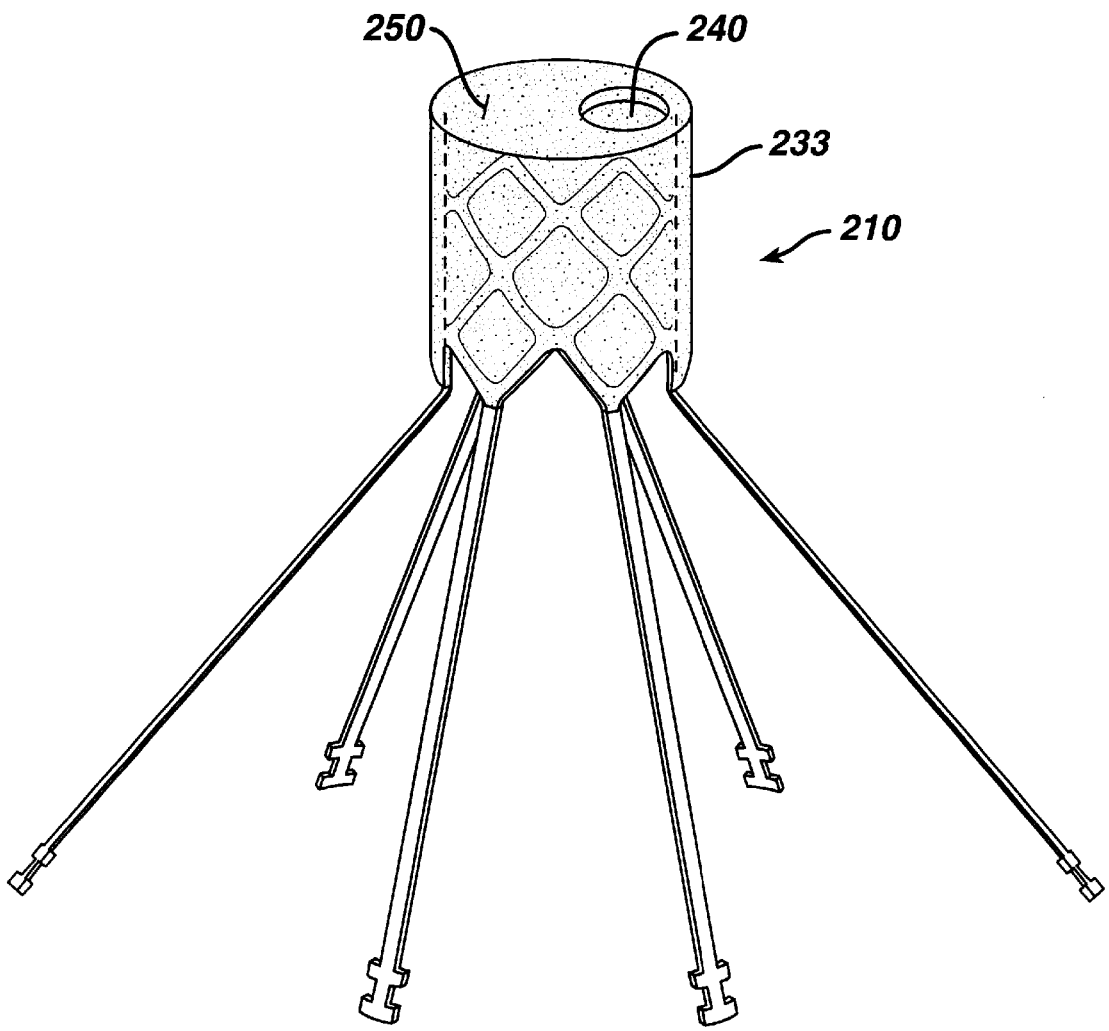
FIG. 8 is a perspective view of an alternative embodiment of a precursor stent made in accordance with the present invention.
Figure 9:
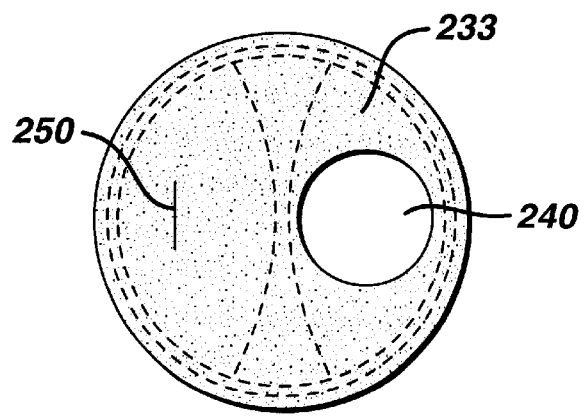
FIG. 9 is a top view of FIG. 8.

An alternative exemplary embodiment of the precursor stent of the present invention is shown in FIGS. 8 and 9. Shown in those figures is precursor stent 210 having an integral gasket member and occlusive member 233. Occlusive member 233 is much like a drum which stretches across the top of the stent and along its sides. Occlusive member 233 has a small opening or slit 250 to accommodate the initial guidewire that it is deployed with, and a larger opening 240 for insertion of the second guidewire after the stent has been deployed.

After the precursor stent 10, with guidewire 92, and guidewire 94 have been deployed and properly positioned within the body, bilateral grafts, similar to that shown in FIG. 12, can then be deployed. Because the guidewires 92 and 94 have been properly placed in the contralateral position, the grafts 80 and 90 will also be placed in the proper contralateral position. That is because graft 80 is guided by guidewire 92 and graft 90 is guided by guidewire 94, and they will follow the paths of their respective guidewires.

Occlusive member 32 may be integral with the gasket member 30. That is the gasket member 30 and occlusive member 32 could be cut from a single piece of material, such as open cell foam, or they could be separate pieces and thereafter attached to each other, member 12 or both using any number of means known to those skilled in the art including a plurality of conventional sutures of polypropylene, DACRON®, or any other suitable material and attached thereto.

Alternately, the gasket member and the occlusive member could take the form of attaching a compressible gasket member, similar to a drum gasket, to the distal end of the expandable member such that it covers only half of the distal end of member 12. As with the gasket member 30, occlusive member 32 can be made from any number of materials known to those of ordinary skill in the art including various polymer materials which are woven, knitted, or foamed to provide a flexible structure such as polyurethane, polyethylene, polytetrafluoroethylene, or other various polymer materials which are woven or knitted to provide a flexible structure such as Dacron, polyurethane, polypropylene, polytetrafluoroethylene.

Figure 11:
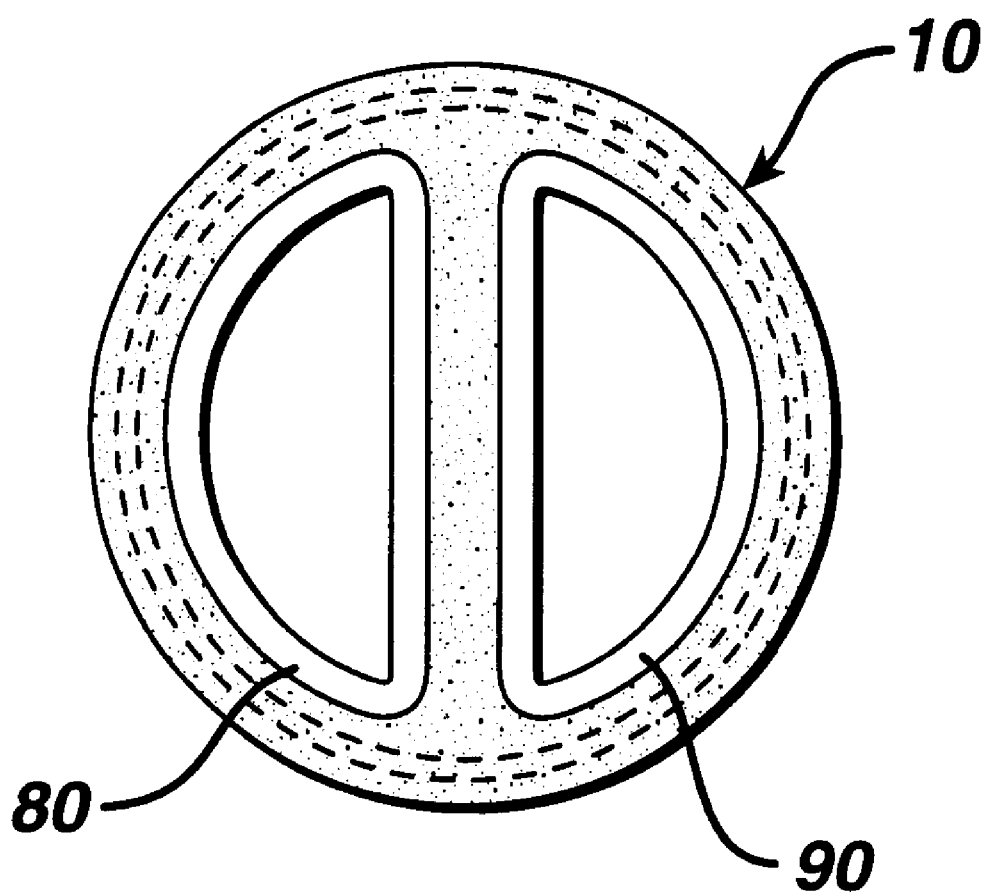
FIG. 11 is a top view of FIG. 10.

Precursor stent 10, acts to temporarily scaffold the gasket member within the body, until the endografts 80 and 90 are deployed. FIG. 11 is a top view of FIG. 10, showing how the endografts form a back to back D-shape configuration when deployed within the precursor stent. Endografts 80 and 90 are typically made from superelastic nitinol, and have enough outward force to stay within the body, without the use of the precursor stent 10. As stated previously, FIG. 8 shows how aneurysm 3 would appear after precursor stent has been fully deployed and two endografts 80 and 90 have been fully deployed as well. Since grafts 80 and 90 are substantially identical, a detailed description of a single endograft, graft 80, will now be given. Endograft 80 has a similar function but a different construction than the graft tube 160 and stent member 162 combination described above. Endograft 80 is preferably comprises a stent 81 laser cut from a tube of material, such as nitinol. The stent has a distal anchoring portion 82, a proximal anchoring stent 84, an middle portion 85 (not shown) and a flexible graft tube 86 covering the middle portion and attached thereto. The stent 81 is expandable from a compressed state to its implanted size. Distal anchoring portion 82 is designed to sealably contact and attach itself to the gasket member 30, and could include legs and flanges attached thereto, so as to make the stent 81 retractable and repositionable similar to stent 10.

Proximal anchoring portion 84 is designed to be expanded so as to make contact with and attach itself to iliac artery 6A Stent 81 is preferably a self-expanding stent, but could also be a plastically deformable balloon expandable stent, both types being discussed above. Graft tube 86 can be made from any of the materials graft member 160 can be made from. Preferred materials include a polymer material woven, spun, knitted, or other fabrication process obvious to those familiar with the art. Graft tube 86 is preferably impermeable to the flow of blood or becomes impermeable to blood flow therethrough after it is saturated. Graft tube 86 must be flexible to contour to the anatomy and of sufficient strength to sustain physiological blood pressure.

FIG. 10 is a good illustration of how the present invention substantially prevents blood from flowing around endografts 80 and 90 and into the abdomen. As seen from that figure, expandable member 12 makes contact with the aorta 2 when it is expanded, and gasket member 30 fills the space between the bilateral endografts 80 and 90 and the aorta 2 thus creating a seal which directs substantially all of the blood flow through the endografts.

Although particular embodiments of the present invention have been shown and described, modification may be made to the device and/or method without departing from the spirit and scope of the present invention. The terms used in describing the invention are used in their descriptive sense and not as terms of limitations.

That which is claimed is:

1. A precursor stent for implantation within the body of a patient, said stent designed to receive a pair of grafts, said stent comprising;
    a) a substantially cylindrical and expandable member having a proximal end, a distal end, a longitudinal axis extending therebetween and an interior; and
    b) an occlusive member attached to said expandable member, said occlusive member occludes about one half of a passageway through said interior of said expandable member, from its distal end to its proximal end, as taken from a plane bisecting said expandable member perpendicular to said longitudinal axis, said occlusive member having an opening extending therethrough.

2. The precursor stent according to claim 1, wherein said expandable member further comprises at least two spaced apart longitudinal legs having distal and proximal ends, said distal ends of said legs attached to said proximal end of said member, said legs extending proximally away from said member, at least one of said legs further including a flange adjacent its proximal end.

3. The precursor stent according to claim 2, wherein said legs extend distally and axially from said expandable member when said precursor stent is deployed within a body.

4. The precursor stent according to claim 2 wherein said at least one flange on said longitudinal legs are substantially I-shaped.

5. The precursor stent according to claim 1 wherein said self-expanding member is made from a superelastic Nickel-Titanium alloy.

6. The precursor stent according to claim 1 wherein said occlusive member is made from a material selected from the group comprising: polyurethane, polyethylene, polytetrafluoroethylene and Dacron.

7. A precursor stent for implantation within the body of a patient, said stent designed to receive and engage a pair of grafts, said stent comprising:
    a) an expandable member having a substantially cylindrical wall, a proximal end, a distal end, a longitudinal axis extending therebetween and an interior, said expandable member further including a gasket member substantially surrounding said wall; and b) an occlusive member attached to said expandable member, said occlusive member occludes about one half of a passageway through said interior of said expandable member, from its distal end to its proximal end, as taken from a plane bisecting said expandable member perpendicular to said longitudinal axis, said occlusive member having an opening extending therethrough.

8. The stent according to claim 7, wherein said expandable member further comprises at least two spaced apart longitudinal legs having distal and proximal ends, said distal ends of said legs attached to said proximal end of said member, said legs extending proximally away from said member, at least one of said legs further including a flange adjacent its proximal end.

9. The stent according to claim 8 wherein said legs extend distally and axially from said expandable member when said precursor stent is deployed within a body.

10. The precursor stent according to claim 8 wherein said at least one flange on said longitudinal legs are substantially I-shaped.

11. The stent according to claim 7, wherein said expandable member is made from a superelastic Nickel-Titanium alloy.

12. The precursor stent according to claim 7 wherein said occlusive member is made from a material selected from the group comprising: polyurethane, polyethylene, polytetrafluoroethylene and Dacron.

13. An aortic graft for intravascular delivery to repair an abdominal aortic aneurysm in an aorta having two iliac arteries associated therewith, said graft comprising:

a) first and second graft members having distal and proximal ends, each graft member is designed to be inserted through a femoral artery in a collapsed condition, and inserted within the aneurysm and deployed therein, said distal ends of said graft members being distal to said aneurysm adjacent an arterial wall; and b) a precursor stent, surrounding said distal ends of each of said graft members and coupled thereto, said precursor stent comprising an expandable member having a substantially cylindrical wall, a proximal end, a distal end, a longitudinal axis extending therebetween and an interior, said expandable member further including a gasket member substantially surrounding said wall and an occlusive member attached to said expandable member, said occlusive member occludes about one half of a passageway through said interior of said expandable member, from its distal end to its proximal end, as taken from a plane bisecting said expandable member perpendicular to said longitudinal axis, said occlusive member having an opening extending therethrough, said precursor stent further including at least two spaced apart longitudinal legs having distal and proximal ends, said distal ends of said legs attached to said proximal end of said member, said legs extending proximally away from said member, each said leg including a flange adjacent its proximal end.

14. The aortic graft of claim 13 wherein said gasket comprises an open cell foam.

15. The aortic graft of claim 13 wherein said precursor stent is made from a superelastic nickel-titanium alloy.

16. The aortic graft according to claim 13 wherein said occlusive member is made from a material selected from the group comprising: polyurethane, polyethylene, polytetrafluoroethylene and Dacron.

* * * * *